(12) United States Patent
Schellekens et al.

(10) Patent No.: US 8,570,037 B2
(45) Date of Patent: Oct. 29, 2013

(54) RF COIL FOR MR IMAGING WHICH IS NOT VISIBLE IN X-RAY IMAGE

(75) Inventors: Wayne Schellekens, Winnipeg (CA); Gordon Scarth, Winnipeg (CA)

(73) Assignee: Imris Inc., Wpg. MB (CA)

( * ) Notice: Subject to any disclaimer, the term of this patent is extended or adjusted under 35 U.S.C. 154(b) by 405 days.

(21) Appl. No.: 12/826,191

(22) Filed: Jun. 29, 2010

(65) Prior Publication Data
US 2011/0050226 A1 Mar. 3, 2011

Related U.S. Application Data

(60) Provisional application No. 61/222,973, filed on Jul. 3, 2009.

(51) Int. Cl.
*G01R 33/48* (2006.01)
*G01R 33/44* (2006.01)

(52) U.S. Cl.
USPC .......................................... 324/309; 324/318

(58) Field of Classification Search
USPC ........................................................ 324/309
See application file for complete search history.

(56) References Cited

U.S. PATENT DOCUMENTS

| | | | |
|---|---|---|---|
| 4,897,788 A * | 1/1990 | King ................................ 378/12 |
| 5,543,712 A * | 8/1996 | Arakawa et al. ............... 324/318 |
| 6,447,888 B2 * | 9/2002 | Suzuki et al. .................. 428/210 |
| 6,925,319 B2 | 8/2005 | McKinnon |
| 7,394,254 B2 | 7/2008 | Rieke |
| 2005/0200550 A1 * | 9/2005 | Vetrovec et al. ............... 343/820 |
| 2005/0284757 A1 * | 12/2005 | Allen ............................ 204/400 |
| 2007/0016003 A1 * | 1/2007 | Piron et al. .................... 600/415 |
| 2008/0088309 A1 * | 4/2008 | Eberler et al. ................. 324/318 |
| 2012/0286786 A1 * | 11/2012 | Schellekens et al. .......... 324/322 |

* cited by examiner

*Primary Examiner* — Patrick Assouad
*Assistant Examiner* — Rishi Patel
(74) *Attorney, Agent, or Firm* — Adrian D. Battison; Ade & Company Inc.

(57) ABSTRACT

An RF coil used for MR imaging is designed so that it remains in place in the field of view of an X-Ray imaging system and comprises a support board on which copper conductive traces and copper printed capacitors are carried. The attenuation of the X-Rays caused by the copper traces is visible in the radiation image but this is compensated by arranging the non-conductive material of the support board such that the attenuation of substantially the whole of the RF coil located within the field of view is substantially constant throughout the field of view.

19 Claims, 4 Drawing Sheets

RF COIL FOR MR IMAGING WHICH IS NOT VISIBLE IN X-RAY IMAGE

This application claims the benefit under 35 U.S.C. 119 of Provisional application Ser. No. 61/222,973 filed Jul. 3, 2009.

This invention relates to an RF coil for use in magnetic resonance imaging which can be used in an Magnetic Resonance Imaging system to obtain MR images of a body part of a patient and can remain in place during X-Ray imaging of the body part without interfering with the X-Ray image.

BACKGROUND OF THE INVENTION

Magnetic resonance imaging (MRI) is commonly employed for medical imaging. In addition, combined use of MRI with radiation (X-Ray) therapy and with radiation imaging have both been used in a number of prior situations. Such systems provide significant advantages compared to single modality systems for obtaining information of the patient. However in such prior dual imaging systems, the patient may need to be moved or transferred from one system to another system. Such transfers can be difficult and time-consuming, and they can compromise results by complicating image registration.

MRI in combination with a radiotherapy accelerator has been used. Thus the X-Rays must be transmitted through the RF coil of the MR imaging system which remains in place during the radiotherapy. Although the RF coils of the MRI system are in the radiation path, they do not cause enough absorption to significantly degrade therapy or require a higher dose for imaging. For example the RF coils may have an equivalent Al thickness of about 2.3 mm, which is sufficiently low for the therapy to be carried out without interference from the coil and low enough to not affect the optimal dose of X-Ray radiation.

Combination of MRI with radiation imaging or more specifically X-Ray imaging cause unique problems. Specifically, if a conventional surface MRI Receive Coil is placed in the imaging path of a X-Ray system, the coil will be visible in the image and may cause artifacts or edges or components of the receive coil may cover important features in the X-Ray image which are required to be seen by the surgeon. For this reason, when MRI is performed in combination with radiation imaging, all coils of the MRI system, including the RF coils, are typically disposed out of or removed from the radiation path so as to be outside the field of view.

For example, U.S. Pat. No. 6,925,319 (McKinnon) issued Aug. 2, 2005 considers a split magnet MRI system having all MRI coils disposed out of the radiation path of an X-Ray system.

Unfortunately, MRI performance can be undesirably degraded by a requirement to place the MRI RF coils outside the field of view of a radiation imaging system. For example, surface RE coils are often placed directly on a subject being imaged for maximum MRI image quality. Such a surface coil is in the field of view of any radiation imaging system that is directed to the same part of the subject as the MRI system. Thus conventional combined MRI and radiation imaging can require an undesirable choice among accepting reduced MRI image quality by placing the RF coils out of the radiation system field of view, accepting RF coil artifacts in the radiation images by placing the RF coils in the radiation system field of view, or by moving the MRI RF coils to one position for MRI imaging and to another position out of the field of view for radiation imaging.

U.S. Pat. No. 7,394,254 (Rieke) issued Jul. 1, 2008 discloses using aluminum for the RF coils to render them "transparent" to X-Ray. More particularly, the patent discloses an arrangement in which improved compatibility of MRI with radiation imaging is provided by MRI RF coils having transmissive coil sections. The transmissive coil sections are substantially transparent to the penetrating radiation employed by the radiation imaging system. Thus the transmissive coil sections can be disposed in a field of view of the radiation imaging system without introducing artifacts into the radiation images. Transparency to penetrating radiation can be achieved by substantially including only low atomic number (i.e., $Z<29$) elements in the transmissive coil sections. Preferably, the transmissive coil sections are fabricated substantially from aluminum.

However it is accepted that the use of aluminum for the traces of an RF coil leads to a degradation in the MR imaging relative to the use of copper. However copper cannot be used in a trace which is sufficiently thin to generate the "transmissive" coil sections of Rieke.

Related disclosures are made in U.S. application Ser. Nos. 12/333,032 filed Dec. 11, 2008 and 12/420,859 filed Apr. 8, 2009 by the present Assignees, the disclosures of which are incorporated herein by reference, which correspond to PCT Applications Serial No: CA2009/000673 and CA2009/000672 both filed May 25, to which reference may be made for further detail.

SUMMARY OF THE INVENTION

It is one object of the present invention to provide an RF coil suitable for use in a dual imaging system using MRI and penetrating radiation such as X-Rays.

According to a first aspect of the invention there is provided Apparatus for use in imaging of a part of a patient using Magnetic Resonance and using penetrating radiation to generate independent images in a field of view of the patient, the apparatus comprising:

a radiation imaging system for generating a radiation image of a subject in the field of view using penetrating electromagnetic radiation; and a magnetic resonance imaging system for generating an image of the subject;

an RF coil for use in the MR imaging system;

the RF coil being arranged to remain in place during the radiation imaging and including coil conductive traces located in the field of view of the radiation imaging;

the RF coil including a support board on which the conductive traces are carried;

the conductive traces of the RF coil being arranged of a conductive material which has a thickness such that the traces cause an attenuation of the penetrating electromagnetic radiation which is visible in the radiation image;

the support board including non-conductive material in the field of view which has a thickness selected such that an attenuation of the penetrating electromagnetic radiation at locations on the board spaced from the traces is substantially equal to the attenuation at locations on the board at the conductive traces.

Preferably the non-conductive material of the support board is arranged relative to the conductive traces such that the attenuation of the penetrating electromagnetic radiation of substantially the whole of the RF coil located within the field of view is substantially constant throughout the field of view. There may however be points or areas where the attenuation is different and an alternative system is used to remove these points or areas from the image. It will be appreciated that such attenuation is not invisible in the image but is instead visible in the sense that it is sufficient to affect the image so that its presence can be determined. However the intention is that the attenuation is constant or homogeneous so that there is no visible artifact within the image and the presence of the RF coil within the image does not affect the changes of image intensity at the various locations within the image which are caused by the differences in attenuation caused by the part being imaged.

In one arrangement, preferably the support board is formed from common material and wherein the thickness of the common material is varied so that the attenuation of the penetrating electromagnetic radiation of substantially the whole of the RF coil located within the field of view is substantially constant throughout the field of view.

In another arrangement, the support board is formed from a base material and an additional material different from the base material is added to the support board.

In both cases the material can be machined to provide the required thicknesses as determined by analyzing the difference in attenuation caused by the materials themselves relative to the copper traces and calculating the required thickness.

Materials can be selected for the additional material or for the board itself which have a very high attenuation so that the thickness of the material is not significantly different from the copper traces.

Conventional techniques and materials for manufacturing the support board can be used including printing the traces or etching the traces as required. Thus the term "traces" is not intended to limit the conductors to any particular method of formation of the conductors on the support board.

Preferably the base material and the additional material are laminated to form a common structure.

Preferably the conductive traces are continuous throughout the field of view so as to have a constant thickness and therefore attenuation. Many techniques are available for forming such continuous traces with out the necessity for joints which may double the thickness at certain locations or may require connecting material such as solder. Thus preferably the conductive traces include no solder within the field of view.

Preferably there are no connector wires from the conductive traces within the field of view so that the connector wires such as coaxial connectors, wires and rods which connect from the traces to the pre-amplifier or other location are located outside the field of view.

In many cases it is necessary to locate the tuning capacitors required for such a coil to be located within the field of view and preferably it is arranged such that the capacitor has an attenuation of the penetrating electromagnetic radiation which is substantially equal to the attenuation of the conductive traces.

This can be achieved where the capacitor is formed from conductive traces with a dielectric material between the traces to define the required capacitance.

In many cases it is also necessary to locate a fuse required for such a coil to be located within the field of view and preferably it is arranged such that the attenuation of the penetrating electromagnetic radiation by the fuse is substantially equal to the attenuation of the conductive traces.

This can also be achieved where the fuse is formed from conductive traces.

Preferably the support board includes no mechanical mounting and support structures within the field of view.

The support board may be flexible.

In many cases it is also necessary to provide a diode for the RF coil and where possible this can be located outside the field of view.

In some cases it is necessary to locate within the field of view a diode or other similar element which has an attenuation different from the conductive traces. In this case the location of the diode in the field of view is arranged to be constant and the image of the diode or other element in the radiation image is removed by software image analysis.

Preferably the conductive traces are formed of copper but other similarly conductive materials can be used instead of aluminum which is effectively transparent to the X-Rays but is generally unsuitable for RF coil manufacture.

The support board can be formed of any suitable non-conductive material which is MR compatible and has an attenuation to X-Rays which is less than or around that of copper such as FR-4 fibreglass circuit board.

DETAILED DESCRIPTION

Figure 1:
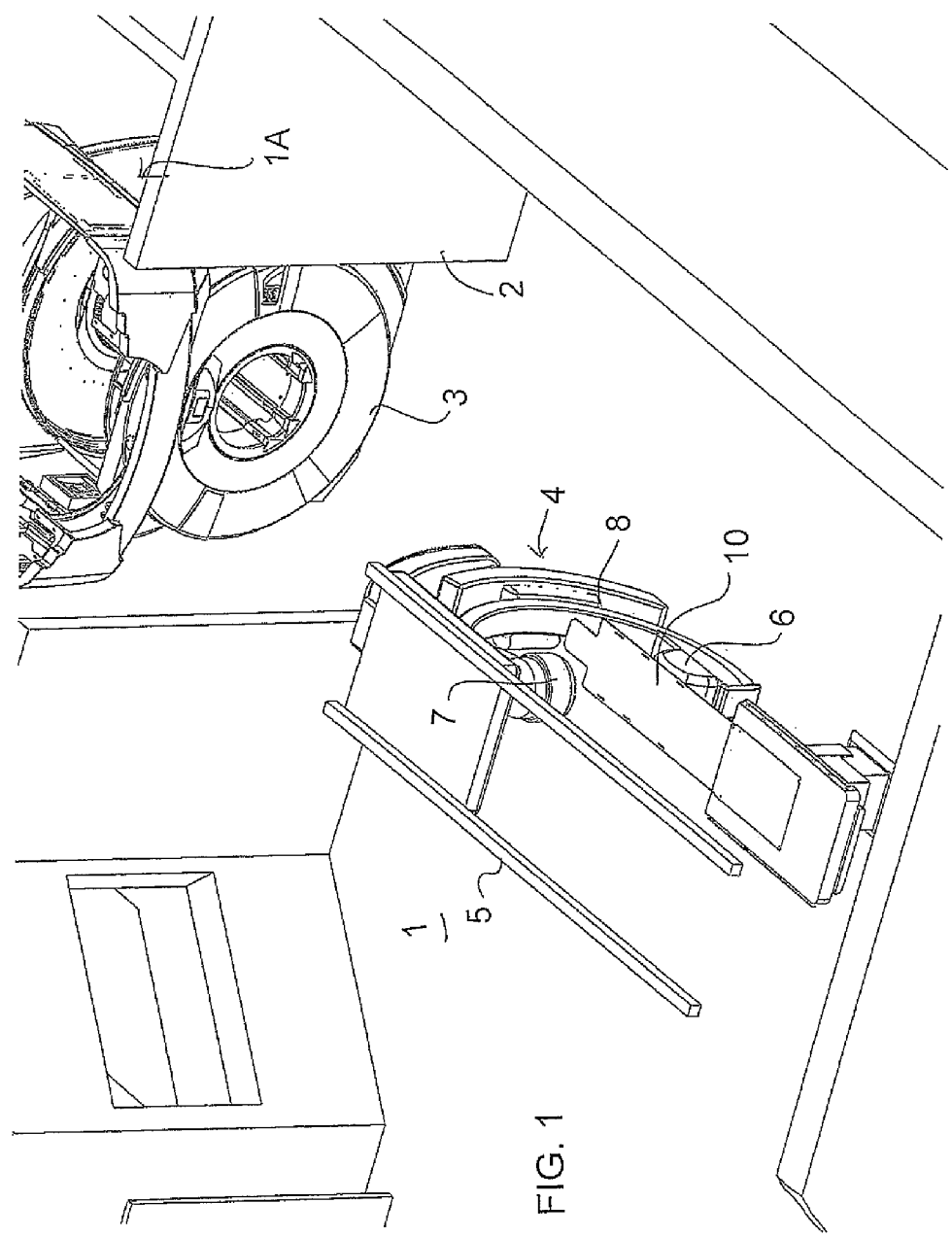
FIG. 1 is an isometric view of an Angiography room showing a patient table, an MRI magnet movable into a position for imaging the patient on the table and an arrangement for moving an X-Ray system.

In FIG. 1 is shown an arrangement for carrying out Magnetic Resonance Imaging and X-Ray imaging of a patient while the patient remains stationary on a patient support table. The arrangement provides a room 1 in which is mounted a patient support table 10 with doors 2 at one side of the room for entry into the room of the magnet 3 of an MR imaging system from a magnet bay 1A. The room contains an X-Ray imaging system 4 mounted on rails 5 and includes an X-Ray transmitter 6 and receiver 7 mounted on a C-shaped support 8. The X-Ray system is of a conventional construction commercially available from a manufacturer such as Siemens. The table 10 described and illustrated herein is used in an arrangement where the patient remains in position on the table while imaging is effected using MRI and X-Ray.

The X-Ray system 4 which co-operates with the moving magnet described above such that the patient can be imaged by either modality on the same table. The patient does not move and at least one of the RF coils remains in place.

The MR is a high-field (e.g. 1.5 T or 3 T or more) magnet that moves on overhead rails between the two or more rooms as described above. In the system described, one or more of these rooms contains an X-Ray system, either a single-plane or a biplane. When the magnet is moved out of the X-Ray examination room and a set of RF and X-Ray shielded doors is closed, the examination room functions as a conventional X-Ray lab and can be used with conventional equipment. In particular, X-Ray guided interventions may be performed.

The arrangement may be used in a typical three room configuration with the Angiography Room (AR) on the left, a Diagnostic Room (DR) in the middle, and an Operating Room on the right. The magnet moves on overhead rails between the rooms and can image in each.

When MR imaging is required, the X-Ray equipment is safely stowed, the doors open, and the magnet is brought into the room over the patient on the table. The RF shield encompasses the AR so all the equipment in the X-Ray examination room is made RE-quiet. MR imaging can then be performed. Afterwards, the magnet is removed from the room, the doors closed, and the X-Ray equipment is returned to its working position.

The MR scanner is used to provide information complementary to that obtained using X-Ray. It can be used, for example, to perform a baseline assessment prior to intervention as well as to perform a post-intervention assessment. Such an assessment may include perfusion and viability studies of, for example, the heart or of the brain.

In the arrangement for moving the X-Ray system as shown in FIG. 1 the MR enters the X-Ray examination room and moves over the head end of the table 10. Since the path of the MR passes right through the location of the C-arm stands, the latter must be moved before the magnet may enter. Depending on need, a floor-mounted C-arm stand may be moved on floor rails, floor turntable, or a boom mounted on the floor or wall. Depending on need, a ceiling-mounted C-arm stand may be moved using extended rails to park it at the foot end of the table, by mounting the stand rails on a platform suspended from the movable magnet rails, or by fixing the stand rails on a platform with a telescopic arm to move them laterally.

Using a solution to move a floor-mounted stand together with a mover for a ceiling mounted stand provides a mechanism to move a biplane system. The mover can provide a mounting position of the single plane or biplane at some non-zero angle to the MR rails, e.g., 90 degrees.

Figure 2:
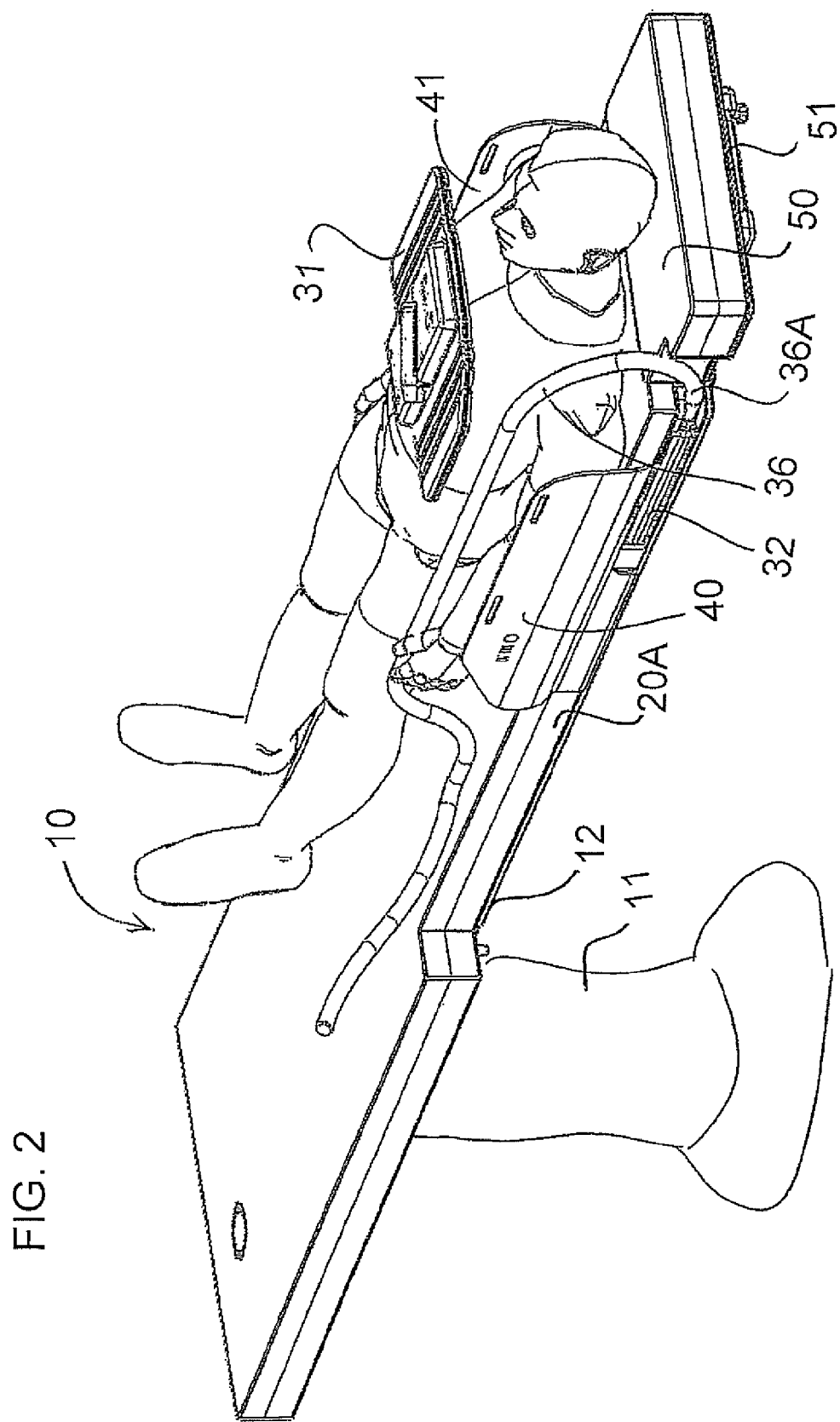
FIG. 2 is an isometric view of a table for mounting the patient, the base being omitted for convenience of illustration, and showing the RF coil construction for imaging of the upper torso of the patient.

The Patient Handling System or support table is shown in FIG. 2 as indicated generally at 10. The patient support table includes a base 11 of a conventional construction which allows the base to move a patient support portion 12 to required locations in height and in orientation. Suitable drive mechanisms and couplings are known in the art and thus are not required to be described herein. At the top of the base 11 is mounted the patient support portion in the form of a generally planar body 12 formed of a fiber reinforced plastics material so as to define a surface area sufficient for supporting the patient while lying on the patient support portion.

When the imaging is to be of the chest, an anterior chest coil 31 is arranged to be placed on top of the chest of the patient when in place for imaging on the mattress and also the posterior coil 32 is arranged to be place behind the patient. Similarly when imaging is to be of the head, coils are placed above and below the head of the patient.

In order to avoid moving the patient when changing from the MR imaging system to the X-Ray imaging system, at least the posterior coil remains in place. Thus this coil will be visible in the X-Ray image. The imaging system may be a simple linear X-Ray system or more preferably is a bi-planar rotating system of the type illustrated which takes multiple images around the patient.

Thus the apparatus for use in imaging of a part of a patient as shown in FIG. 1 includes the radiation imaging system 4 for generating a radiation image of a subject in the field of view using penetrating electromagnetic radiation and the magnetic resonance imaging system for generating an image of the subject including the magnet 3 and the RF coils 31, 32.

Figure 3:
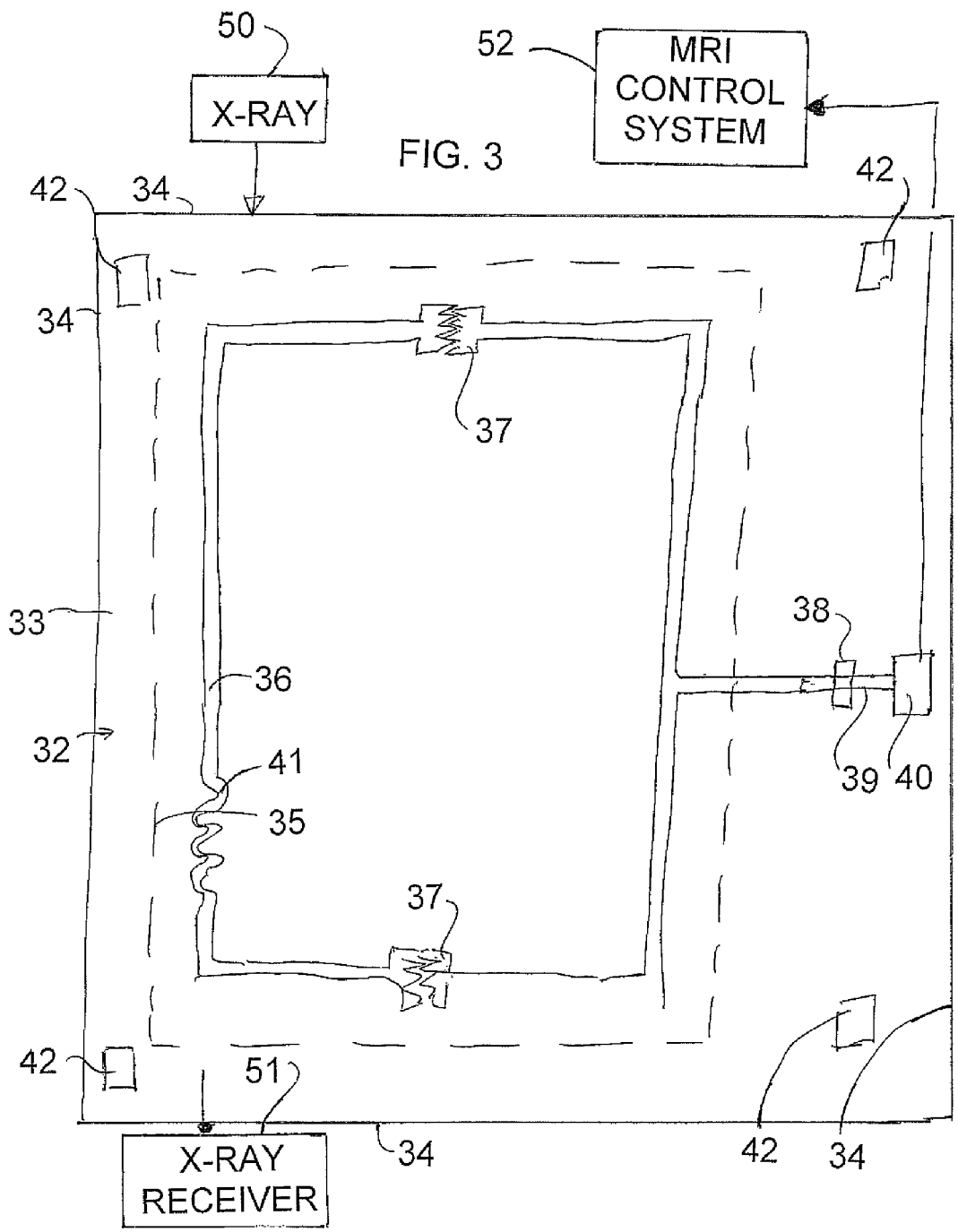
FIG. 3 is a plan view of the RF coil including the components of the system attached thereto which are shown schematically.
Figure 4:
FIG. 4 is a cross sectional view through the RF coil.

A schematic illustration of the RF coil 32 is shown in FIGS. 3 and 4 and is arranged to remain in place during the radiation imaging using the X-Ray transmitter 50 and receiver 51 shown only schematically.

The RF coil includes a support board 33 having side edges 34 and the imaging system 4 defines a field of view 35 within the area of the board which can be seen in the X-Ray image with portions of the board outside the field of view being outside the image.

The circuitry of the coil includes conductive traces 36, capacitors 37, a fuse 41, a diode 38, a connecting wire 39, and a pre-amplifier 40. All of these elements are conventional in general construction and are well known to persons skilled in the art of coil design so that detailed explanation is not required here.

The conductive traces of the RF coil are arranged of a conductive material and typically copper which has a thickness T3 of at least 0.0007 inch and preferably in the range 0.0014 inch to 0.0042 inch which is effective to receive the RF signals from the MR imaging system. Such traces typically cause an attenuation of the penetrating electromagnetic radiation which is clearly visible in the radiation image as compared with a uniform thickness support board material.

As shown in FIG. 4, the support board is formed of a non-conductive material in the field of view which has a thickness T1 at locations on the board spaced from the traces selected such that an attenuation of the penetrating electromagnetic radiation at those locations is substantially equal to the attenuation at the conductive traces. Thus the attenuation of the board material at thickness T1 is arranged so that it is equal to the sum of the attenuation caused by the thickness T3 of the trace and thickness T2 of the board at the trace. In this way the attenuation of the penetrating electromagnetic radiation of substantially the whole of the RF coil located within the field of view is substantially constant throughout the field of view.

While the traces are shown in FIG. 4 recessed into shallow areas of the board, the traces can be applied on top of the flat board and the variable thickness of the board applied at the rear. In addition, the board may be flat by filling recesses with a material which is transparent to X-Ray and thus does not affect the attenuation.

Figure 5:
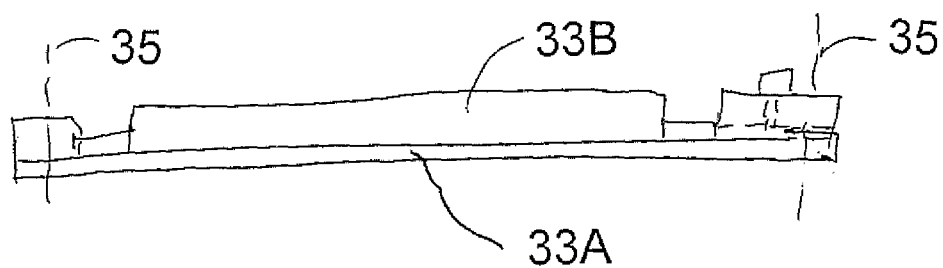
FIG. 5 is a cross sectional view through the RF coil showing a modified construction.

In FIG. 5 is shown an alternative arrangement in which the board is formed of a base material 33A and an additional material 33B is added to the support board at areas separate from the traces, which material is non-conductive and has an attenuation factor that is it is not transparent to X-Ray and is different from the base material 33A. The base material and the additional material are laminated to form a common structure and the recesses may be filled by additional transparent material.

The conductive traces are arranged to be continuous throughout the field of view so as to have a constant attenuation. That is the conductive traces include no joints and therefore no solder within the field of view. Instead the traces are printed or otherwise applied as a constant continuous strip. Alternatively the traces are formed by etching away unwanted material from a continuous layer on the board leaving traces which are continuous and without joints.

As shown in FIG. 3 all connector wires 39 from the coil are located outside the filed of view 35 there are no connector wires from the conductive traces within the field of view.

The capacitors 37 and the fuse 41 for the coil are in most cases necessarily located within the field of view 35 and these are therefore arranged so that the attenuation of the penetrating electromagnetic radiation is substantially equal to the attenuation of the board at the conductive traces. Thus the capacitor and the fuse is itself formed from conductive traces which are designed and laid out on the board with the required amount of conductive material and the dielectric material to provide the required characteristics and values. The design of such components from conductive traces is known and within the skill of a person skilled in this art.

The support board includes mechanical mounting and support structures 42 for connection of the board to necessary elements but these are designed and arranged so that they are outside the field of view so that the board is generally constant and continuous and there are no mechanical structures within the field of view.

The necessary diode 38 is designed and arranged on the traces so that it is located outside field of view.

As an alternative, the diode or other necessary element is located within the field of view where the element has an attenuation different from the conductive traces and of a construction and high attenuation factor such that it cannot reasonably be compensated for by building the remainder of the board up to this high attenuation factor. In this arrangement, where element is located in the field of view, the location of the element in the field of view is constant and the image of the element in the radiation image is removed by software image analysis at the X-Ray receiver system 51.

The invention claimed is:

1. Apparatus for use in imaging of a part of a patient using Magnetic Resonance and using penetrating radiation to generate independent images in a field of view of the patient, the apparatus comprising:
    a radiation imaging system for generating a radiation image of a subject in the field of view using penetrating electromagnetic radiation; and
    a magnetic resonance imaging system for generating an image of the subject;
    an RF coil for use in the MR imaging system;
    the RF coil being arranged to remain in place during the radiation imaging and including coil conductive traces located in the field of view of the radiation imaging system;
    the RF coil including a support board on which the conductive traces are carried;
    the conductive traces of the RF coil being arranged of a conductive material which has a thickness such that the traces cause an attenuation of the penetrating electromagnetic radiation which is visible in the radiation image;
    the support board including non-conductive material in the field of view which has a thickness selected such that an attenuation of the penetrating electromagnetic radiation at locations on the board spaced from the traces is substantially equal to the attenuation at locations on the board at the conductive traces.

2. The apparatus according to claim 1 wherein the non-conductive material of the support board is arranged relative to the conductive traces such that the attenuation of the penetrating electromagnetic radiation of substantially the whole of the RF coil located within the field of view is substantially constant throughout the field of view.

3. The apparatus according to claim 2 wherein the support board is formed from common material and wherein the thickness of the common material is varied so that the attenuation of the penetrating electromagnetic radiation of substantially the whole of the RF coil located within the field of view is substantially constant throughout the field of view.

4. The apparatus according to claim 2 wherein the support board is formed from a base material and an additional material different from the base material is added to the support board so that the attenuation of the penetrating electromagnetic radiation of substantially the whole of the RF coil located within the field of view is substantially constant throughout the field of view.

5. The apparatus according to claim 4 wherein the base material and the additional material are laminated to form a common structure.

6. The apparatus according to claim 1 wherein the conductive traces are of constant thickness throughout the field of view so as to have a constant attenuation.

7. The apparatus according to claim 1 wherein the conductive traces include no solder within the field of view.

8. The apparatus according to claim 1 wherein there are no connector wires from the conductive traces within the field of view.

9. The apparatus according to claim 1 wherein there is provided within the field of view at least one capacitor which has an attenuation of the penetrating electromagnetic radiation which is substantially equal to the attenuation of the conductive traces.

10. The apparatus according to claim 9 wherein the capacitor is formed from conductive traces.

11. The apparatus according to claim 1 wherein there is provided within the field of view a fuse which has an attenuation of the penetrating electromagnetic radiation which is substantially equal to the attenuation of the conductive traces.

12. The apparatus according to claim 11 wherein the fuse is formed from conductive traces.

13. The apparatus according to claim 1 wherein the support board includes no mechanical mounting and support structures within the field of view.

14. The apparatus according to claim 1 wherein the support board is flexible.

15. The apparatus according to claim 1 wherein there is provided a diode which is located outside field of view.

16. The apparatus according to claim 1 wherein there is provided within the field of view at least one element which has an attenuation different from the conductive traces, where the location of the element in the field of view is constant and the image of the element in the radiation image is removed by software image analysis.

17. The apparatus according to claim 1 wherein there is provided within the field of view a diode which has an attenuation different from the conductive traces, where the location of the diode in the field of view is constant and the image of the element in the radiation image is removed by software image analysis.

18. The apparatus according to claim 1 wherein the conductive traces are formed of copper.

19. The apparatus according to claim 1 wherein the support board is formed of FR-4.

\* \* \* \* \*